US006402986B1

(12) United States Patent
Jones, II et al.

(10) Patent No.: US 6,402,986 B1
(45) Date of Patent: Jun. 11, 2002

(54) COMPOSITIONS AND METHODS FOR LUMINESCENCE LIFETIME COMPARISON (75) Inventors: Guilford Jones, II, Canton; Dingxue Yan, Quincy, both of MA (US)

(73) Assignee: The Trustees of Boston University, Boston, MA (US)

( * ) Notice: Subject to any disclaimer, the term of this patent is extended or adjusted under 35 U.S.C. 154(b) by 0 days.

(21) Appl. No.: 09/354,891

(22) Filed: Jul. 16, 1999

(51) Int. Cl.[7] .............................. C09K 11/06; G09C 5/00
(52) U.S. Cl. ...................... 252/301.16; 428/690; 427/7; 427/157; 283/74; 250/459.1
(58) Field of Search .................. 250/459.1; 252/301.16, 252/301.34, 301.35; 428/690; 427/7, 157; 283/74

(56) References Cited

U.S. PATENT DOCUMENTS

| 4,061,578 A | 12/1977 | Kleinerman ................. 250/330 |
| 4,202,491 A | 5/1980 | Suzuki ......................... 235/491 |
| 4,283,382 A | 8/1981 | Frank et al. .................... 424/8 |
| 4,311,914 A | 1/1982 | Huber ......................... 250/556 |
| 4,463,970 A | 8/1984 | Kaule, et al. .................. 283/72 |
| 4,464,787 A | 8/1984 | Fish et al. ...................... 382/7 |
| 4,507,349 A | 3/1985 | Fromson et al. ............. 428/195 |
| 4,540,595 A | 9/1985 | Acitelli et al. ................. 427/7 |
| 4,652,143 A | 3/1987 | Wickersheim et al. ...... 374/161 |
| 4,752,141 A | 6/1988 | Sun et al. .................... 374/161 |
| 4,819,658 A | 4/1989 | Kolodner .................... 128/736 |
| 4,837,169 A | 6/1989 | Toner ......................... 436/546 |
| 4,859,777 A | 8/1989 | Toner ......................... 546/256 |
| 4,877,965 A | 10/1989 | Dandliker et al. ......... 250/458.1 |
| 4,954,714 A | 9/1990 | Pollak et al. ............. 250/458.1 |
| 4,983,817 A | 1/1991 | Dolash et al. .............. 235/462 |
| 5,005,873 A | * 4/1991 | West ............................ 283/92 |
| 5,039,219 A | 8/1991 | James et al. ................. 356/318 |
| 5,093,147 A | 3/1992 | Andrus et al. ................. 427/7 |
| 5,158,703 A | * 10/1992 | Takuma et al. ......... 252/301.35 |
| 5,281,825 A | 1/1994 | Berndt et al. ............. 250/458.1 |
| 5,304,809 A | 4/1994 | Wickersheim ........... 250/458.1 |
| 5,323,008 A | 6/1994 | Studholme et al. ...... 250/458.1 |
| 5,351,268 A | 9/1994 | Jensen et al. ............... 374/131 |
| 5,360,628 A | 11/1994 | Butland ........................ 427/7 |
| 5,414,266 A | 5/1995 | Sun ......................... 250/459.1 |
| 5,464,986 A | 11/1995 | Boettcher et al. ........ 250/459.1 |
| 5,502,304 A | 3/1996 | Berson et al. .............. 250/271 |
| 5,514,860 A | 5/1996 | Berson ........................ 235/468 |
| 5,523,573 A | 6/1996 | Hänninen et al. ........ 250/459.1 |
| 5,525,798 A | 6/1996 | Berson et al. .............. 250/271 |
| 5,542,971 A | 8/1996 | Auslander et al. ......... 106/21 A |
| 5,543,971 A | 8/1996 | Nomura et al. ............. 359/697 |
| 5,591,981 A | 1/1997 | Heffelfingr et al. ...... 250/458.1 |
| 5,622,821 A | 4/1997 | Selvin et al. .................... 435/6 |
| 5,656,433 A | 8/1997 | Selvin et al. .................... 435/6 |
| 5,693,693 A | * 12/1997 | Auslander et al. ........ 106/31.14 |
| 5,837,042 A | * 11/1998 | Lent et al. ................ 106/31.14 |
| 5,854,008 A | 12/1998 | Diamandis ................. 435/7.91 |
| 5,861,618 A | 1/1999 | Berson ........................ 235/468 |
| 6,030,657 A | * 2/2000 | Butland et al. ................. 427/7 |

* cited by examiner

Primary Examiner—C. Melissa Koslow
(74) Attorney, Agent, or Firm—Weingarten, Schurgin, Gagnebin & Lebovici LLP (57) ABSTRACT

This patent disclosure describes novel compositions and methods used in the verification of products or documents based on the reading of emitted light from luminescent compositions that can be incorporated or applied to a wide variety of materials. Specifically, the compositions are uniquely luminescent at various wavelengths, displaying qualities of image, wavelength, and time scale for the measure of luminesce decay. The light emitted from the composition, and specifically, the measure of the variable and adjustable luminescence lifetimes provides a multi-parameter signature for purposes of comparative light decay analysis of verification marks or features.

10 Claims, 6 Drawing Sheets

COMPOSITIONS AND METHODS FOR LUMINESCENCE LIFETIME COMPARISON

FIELD OF THE INVENTION

The present invention relates to novel compositions and methods that are of use in the verification of products or documents. The compositions and methods are based on the reading of emitted light from luminescent compositions that can be incorporated or applied to a wide variety of materials.

BACKGROUND

Accurate verification of products and documents is critical to a wide variety of industries including the manufacture of pharmaceutical, clothing, automotive parts, and the issuance of credit and identification cards or travel/immigration documentation. Counterfeiters of products, currency and documents have developed increasingly sophisticated methods of detecting and copying of marks and labels.

Counterfeiting and product diversion cost owners of products, brand names, and intellectual property billions of dollars annually on a world-wide basis, according to the International Anti-Counterfeiting Council (IACC). The problem in the United States, for example, encompasses an estimated loss in revenues of $200 billion per year, as well as associated costs in tax revenues and the loss of jobs.

Current technologies being used to address this problem are varied. The use of chelates as security markings is described in U.S. Pat. No. 5,837,042 to Lent et al. However, the patent is limited because it fails to describe any chelate ligands beyond the class of 1,3-diketones or salicylic acid. Also, the patent only uses the chelates in ink jet printing applications. Therefore, this invention is limited to very specific applications. Also, the 1,3-diketone ligands do not show long term stability to light. In common use, this is an important consideration, because labeled or marked goods or documents are subjected to changes in temperature, humidity, exposure to light, and other environmental perturbations.

Accordingly, there is a continuing need to develop new compositions and methods for product verification and security identification of goods and documents in common use.

SUMMARY OF THE INVENTION

As a solution to the above-related deficiencies in the prior art, the present invention is directed to comparing luminescent markings of novel chelates for a variety of substrates, such as paper (e.g. currency, stocks, bonds), cloth (or threads), plastic (e.g. plastic cards), leather, metal, glass, or other convenient forms may be used. These markings provide a code that is read as an image, a wavelength (color), and a luminescent decay time. The new chelates show superior absorption and energy transfer features, particularly for sensitizing the luminescence of europium and terbium metals. In addition, the new chelates have a high stability toward photochemical decomposition rate. Moreover, a class of luminescence lifetime modifiers (e.g. derivatives of imidazole that serve as ancillary coordinating ligands), is used in conjunction with a variety of chelates in order to produce a matrix of variables that include emission wavelength and decay time. It is further contemplated that a combination of one or more compositions having variable lifetimes can be scanned for recording wavelength and decay time with high fidelity. Also described is a simple inexpensive detector that is used for the collection and communication of luminescence data.

The present invention contemplates light-based technology that introduces varied levels of discrimination for covert markings or labels that is incorporated into, or applied to, most products of commercial interest. The present invention comprises compositions that have been successfully used to invisibly label fabrics, including cotton, wool, and synthetic fibers, and leather goods. These dyes have also been successfully applied to glass and metal surfaces, as well as incorporated into plastics. The invisible labels are not limited to overt application. Rather, the present invention contemplates marking surfaces in a covert manner such that resultant marks, labels, or bar codes are invisible to the naked eye in normal lighting.

Specifically, the compositions are uniquely luminescent at various wavelengths, and allow for a comparison that utilizes the composition's unique qualities of image, wavelength, and time scale in order to detect the light emitted from the composition. Measurement of the luminescence decay lifetime provides unique "fingerprints" of the luminescent compositions, for purposes of comparative analysis. Luminescence decay lifetimes are variable, and are reproducible and adjustable with the addition of luminescence lifetime modifiers to the compositions, which provide for multivariate lifetime imaging.

In one embodiment of the present invention, luminescence intensities of compositions are recorded as a function of time following initiating pulses of light. Wavelength and time resolution of the luminescence signals produce a unique 'fingerprint' for any composition that is associated with a product or document. This coding of luminescence information can be employed in bars, strips, or layers, and as single features of various shape, or as one and two dimensional arrays. These features can be detected using a scanning device that can store or transmit data for recovery and use in the verification of product or document identity. The compositions display discrete luminescence signals whose decay times are an adjustable variable that depends on the selected metal, the chelating ligand, and modifying agents that provide further control over luminescence lifetime.

In another embodiment of the present invention, these luminescent compositions are doped into materials or on surfaces using solvents as carriers. These compositions can be applied to a variety of materials including paper, card stock, plastic packaging or surfaces, and fabric by brushing, dipping, spraying, aerosol application, writing instruments, or through the use of a conventional inkjet photocopier or devices which employ nozzle feeding mechanisms. Detectable luminescent marks have been demonstrated on materials that include threaded or woven organic materials, credit cards, paper, ink-jet prints, plastic packaging and parts, and metal surfaces. The compositions absorb in the near ultraviolet region (300–400 nm), and are capable of producing readily detected luminescence in the visible (blue, green or red) in relatively narrow bands.

The compositions of the present invention exhibit delayed luminescence, a process of light emission that is normally much less efficient than the commonly observed fluorescence associated with many colored materials. When these two types of emission are time-resolved, normal fluorescent light appears in the time domain of nanoseconds ($10^{-9}$ second), following an initiating light pulse. The processes of long lived luminescence, known as delayed fluorescence or phosphorescence, are active in the time domain of microseconds to seconds (and occasionally longer times). Delayed fluorescence or phosphorescence, on the other hand, occurs on a time scale that is sufficiently slow that detection apparatus based on less sophisticated electronics or on mechanical "chopping" will suffice.

In an embodiment of the present invention, the reading of specific wavelengths of emitted light, or the comparison of luminescent images through the use of any number of light photodetectors, including spectrometers, florimeters, and phosphorimeters is contemplated.

The luminescent signals, referred to as "fingerprints", are unique to a given composition and the substrate to which it is applied. While it is not intended that the present invention be limited to any specific device by which delayed luminescence can be compared, in one embodiment of the present invention, the detection and comparison of wavelengths would be achieved using a variety of commercially available instruments. For example, the detection of luminescent radiation, in the recording of steady state emission and excitation spectra, can be carried out using a Photon Technology International, Inc., QuantaMaster luminescence spectrometer, model SE-900M. Emission lifetimes can be measured using a PTI TimeMaster fluorescence lifetime spectrometer, equipped with a GL-3300 nitrogen/dye laser as the excitation source (e.g. $\lambda exc=337$ nm), a DG-535 delay/pulse generator and a strobe detector. Similar instruments, also capable of measuring luminescence decay times in the range from 100 ps to seconds are also available from other vendors (e.g. Edinburgh Analytical Instruments FS900 spectroflourimeter system). These commercial instruments can be configured to record luminescence spectra and luminescence excitation spectra for the entire range of ultraviolet, visible and infrared wavelengths (e.g. 200–900 nm). Software available from the fluorimeter vendors is capable of decay time analysis including, for example, the computation of luminescence lifetimes, the determination of multiple exponential decay functions, and a statistical analysis of goodness-of-fit to the decay data.

In another embodiment, the comparison of luminescence may be carried out using devices of simple design that allow portability and ease of operation by personnel having minimal training in the field of luminescence spectroscopy. For example, a compact hand-held apparatus can be fabricated that incorporates a readily available emitting diode light source, and inexpensive diode detector, and simple circuity that can be understood and implemented by persons skilled in the art of detector electronics. Such a device is illustrated in the description of a UV-scanning apparatus, constructed from available optical and electronic components, that has the capability of discriminating slow-decaying luminescence. These components include a very low-leakage Hamamatsu photodiode (R2506-02), a high impedance (10–12 ohm) FET operational amplifier (TLO 64), CMOS analog switches (74HC 4066), and a MOSFET low on resistance transistor (IRF 7503) for UV modulation. Utilizing a double differential scheme, the apparatus is relatively insensitive to ambient light and/or temperature changes. Extremely weak signals of luminescence can be sensed by the low-leakage photodiode, if signals are amplified and averaged over multiple periods of the clock generator (LM311) to improve the signal/noise ratio.

In another embodiment of the present invention, the coding of luminescence information is detected using a scanning device that can store or transmit data for recovery and use in the verification of product or document identity. The storage and transmission of data for recovery may be accomplished via any type of cable or wire, and is not limited to any particular distances. Rather, the present invention may be used to achieve the storage and transmission of data for recovery from one physical point to one or several other specified locations.

In another embodiment of the invention, chelate-luminescence lifetime modifier compositions offer unique combinations of luminescence, durability, long shelf life, and a high level of difficulty with regard to counterfeit reproduction.

In a further embodiment of the present invention, the marking system can be rotated, or "turned over" on a timely basis through a systematic tuning of the luminescent tags such that the delay-time intervals for comparison are variable, as well as the wavelengths of emitted light.

In another embodiment of the present invention, the specific wavelength signals of emitted light can be read using photodetectors, and then transmitted via cable or telephone wires, and stored or compared at a distal site.

In another embodiment of the present invention, novel chelate/substrate combinations are contemplated. Such combinations comprise the use of any substrate, such as paper (e.g. plain, colored, currency, checks, stocks, bonds), cloth, plastic, leather, thread, metal, glass, or other convenient form, used in conjunction with a metal from the lanthanide series of chemical elements. The present invention does not limit the metal to the lanthanide series of chemical elements. A variety of metal elements are contemplated, and the compositions of the present invention. may comprise any type of metal elements.

DESCRIPTION OF THE DRAWINGS

Structures are assumed to be tris-chelates in which three ligands are bound to the metal; the appropriate counterion (e.g. sodium) is not shown.

DEFINITIONS

To facilitate understanding of the invention, a number of terms are defined.

The term "luminescence" refers to emitted radiation that results from de-excitation of a molecule or ion from an excited electronic state to its ground electronic state. The emitted radiation is referred to as fluorescence if the excited and ground electronic states are of the same spin multiplicity (de-excitation does not require a change in spin angular momentum); the emitted radiation is known as phosphorescence if de-excitation is "spin forbidden" does require a change is spin in angular momentum. Luminescence is a process that normally requires the absorption of light at one wavelength, resulting in excited species which are fluorescent or phosphorescent at a different (longer) wavelength; R. S. Becker, "Theory and Interpretation of Fluorescence and Phosphorescence," Wiley-Interscience, pages 76–97, New York, 1969.

The term "luminescent compound" for the purposes of the present invention, refers to a substance that is capable of emitting electromagnetic radiation as the result of photoexcitation.

For the purposes of this invention, we define luminescence as "short-lived" if the decay time associated with that emission is shorter than 0.1 microsecond and "long-lived" if the decay time is longer than 0.1 microsecond. It is understood, although not strictly required, that these ranges of time scale can be defined, respectively, as fluorescence and phosphorescence. In general, the more inclusive term that defines emitted radiation, luminescence, will be used in describing essential elements of the current invention.

The term "luminescence decay time" refers to the profile of luminescence intensity as a function of time for a composition that gives rise to fluorescence or phosphorescence, and may interchangeably be referred to herein by the term "fingerprint", to signify the particular profile of any specific composition. The luminescence of any composition will grow and decay in a particular period of time with respect to an initiating light pulse; the decay profile will be a particularly sensitive characteristic of the specific composition or combination of composition and chemical environment in which that composition is bound; J. N. Demas, "Excited State Lifetime Measurements," Academic Press, pages 12–42, New York, 1983. The luminescence decay can be plotted graphically as an intensity versus time plot, and subjected to mathematical analysis that allows a quantitative description of the shape and decent of the decay curve. Most commonly, a luminescence decay will follow an exponential function; however, the decay pattern may be more complex, reflecting the possible array of compositions that display different properties of the composition, or different physical environments. More complex decay functions that can be shown to fit an observed luminescence decay pattern include multiple exponentials (double, triple, etc.), a "stretched exponential", a Gaussian distribution of exponentials, or other complex functions J. N. Demas, supra.

Figure 2:
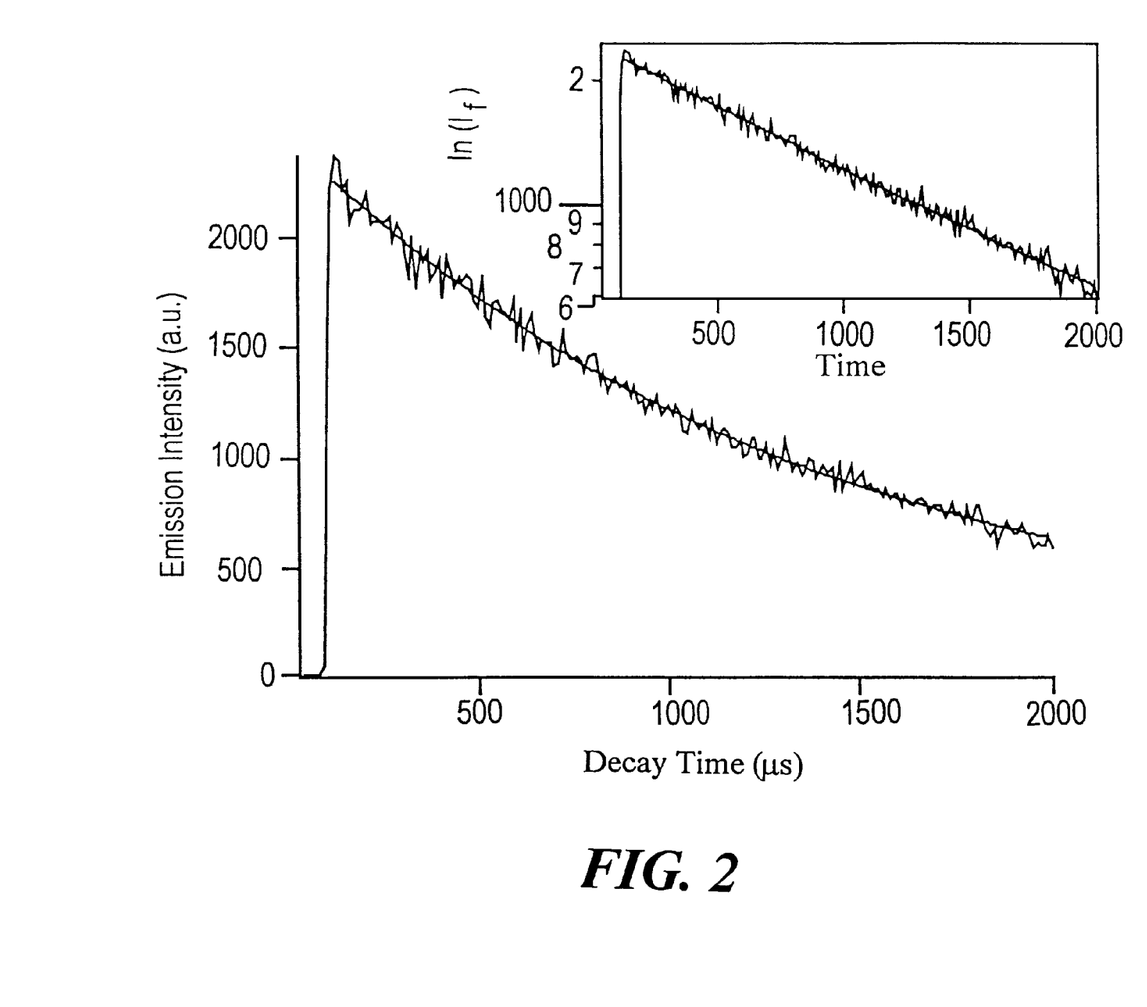
FIG. 2 is a plot of luminescence decay time for chelate 4 on paper (water medium, pH 8.5); $\lambda_{exe}=337$ nm, $\lambda_{lum}=615$ nm.

The decay time, as it is defined, is a characteristic of the luminescent compositions of the present invention. In one embodiment, luminescence from a marked substrate will follow a single exponential decay. In the accompanying FIG. 2, the luminescence of chelate 4 is shown, along with the identification of the material that is marked and the experimental conditions used for observation. The parameters associated with this embodiment are (a) the intensity profile, (b) the log plot of intensity vs. time that is a linear function for a single exponential (FIG. 2), and (c) a luminescence lifetime (having the symbol, $\tau 1um$) that results from the slope of the log plot or from other curve fitting procedures. In other embodiments, luminescence follows a decay pattern that is described best by two exponentials. The double exponential behavior can be illustrated with a log plot; two decay times, $\tau 1$ and $\tau 2$, result from analysis of two linear portions of this type of graph; J. N. Demas, supra. In other embodiments, the decay time of a luminescent species can be expressed as lifetimes associated with single or multiple exponentials ($\tau 1$, $\tau 2$, $\tau 3$, etc.) or with parameters associated with stretched exponential fits or gaussian distributions of lifetimes, or simply as a weighted or unweighted average of the various distributed quantities.

Figure 1:
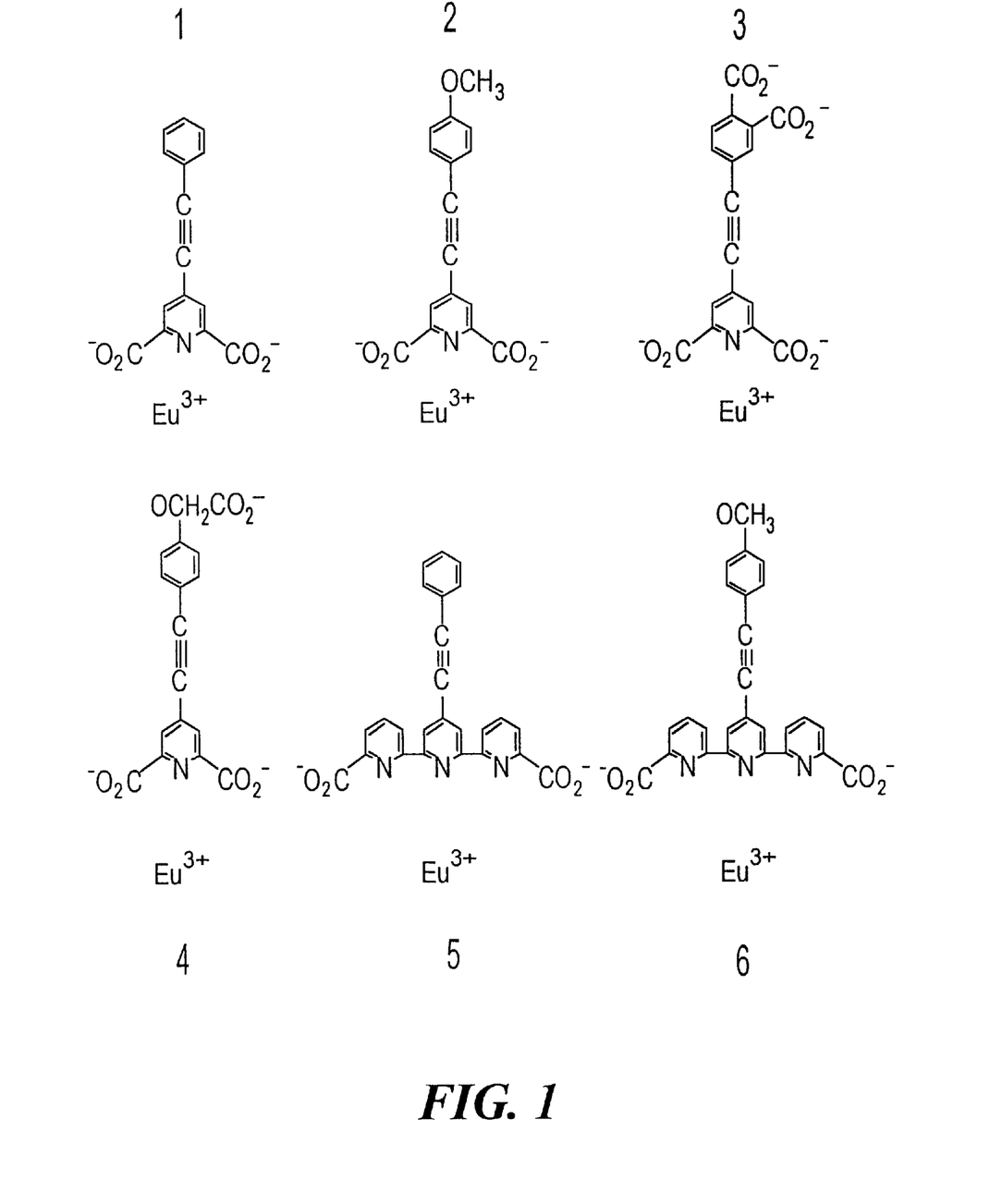
FIG. 1 displays europium chelates 1–6, in which the chemical structures of the ligands are illustrated (the chelates comprise the europium/ligand structure).

The term "chelate" as defined herein, is a compound comprising a metal/non-metal combination of compound (e.g. the europium/ligand structure of FIG. 1).

The term "lanthanide chelate" as defined herein, is a compound comprising a metal from the lanthanide series of chemical elements that is coordinated to one or more ligands. "Ligand" is defined as an organic or inorganic molecule or ion that is capable of chemical coordination to a metal. Examples of ligands include, but are not limited to, 1,3-diketones, heterocyclic compounds, including the bi- and terpyridines, polycyclic azaaromatic compounds, dipicolinic acid, coumarins, phenols, and salicylic acids. These ligands are normally capable of taking up two or more coordination sites if on the metal. The present invention does not limit the metal to the lanthanide series of chemical elements. A variety of metal elements are contemplated, and the compositions of the present invention may comprise any type of metal elements.

The term "luminescence lifetime modifier" refers to a chemical agent that is capable of altering (as measured using procedures in the present specification) the emission lifetime (i.e. decay time) of a sample containing a luminescent compound. Examples of luminescence lifetime modifiers include, but are not limited to, imidazole, analogs of imidazole, and derivatives of imidazole. The term "luminescence enhancer" refers to a luminescence lifetime modifier that enhances the luminescence of a luminescent compound when tested under the conditions described herein.

The term "substrate" as used herein, refers to a material having a rigid or semi-rigid surface. Such materials will preferably take the form of organic or inorganic materials, such as paper (e.g. colored, plain, currency, stocks, bonds), plastic, leather, cloth, thread, metal, and glass, or other convenient forms may be used. In some embodiments, at least one surface of the substrate will be substantially flat. A substrate may be marked, labeled, tagged or otherwise designated or sorted as the result of application of a luminescent composition of the present invention.

The term "metal" as used herein, refers to a metal center, a metal ion, or a metal element, without regard to any specific oxidation state.

DESCRIPTION OF THE INVENTION

A number of different classes of dyes can give rise to the long-lived luminescence (ms time domain) that is required in the present invention to distinguish luminescent marks on products, goods, or apparatus. Classes of organic dyes that give rise to phosphorescence in the appropriate time domain include, but are not limited to, coumarin, triarylmethane, cyanine, phthalocyanine, quinone, anthraquinone, polycarbonyl, xanthene, rhodamine, acridine, and phenazine dyes. Transition metal complexes include, but are not limited to, the complexes or chelates of chromium or ruthenium, and also give rise to long-lived luminescence. While it is also not intended that the present invention be limited to the particular compositions or methods herein described, the present invention contemplates use of particular compositions comprising a ligand-lanthanide chelate, a solvent, and a luminescence lifetime modifier. The present invention also contemplates methods by which the luminescent compositions are compared. Specifically, the present invention contemplates a method comprising: providing one or more substrates; one or more luminescent compositions, and a device for detecting the luminescence of the compositions: adding the compositions to the substrates, detecting the luminescence of the substrates by using a device, and comparing the luminescence emitted from the substrates.

Figure 5:
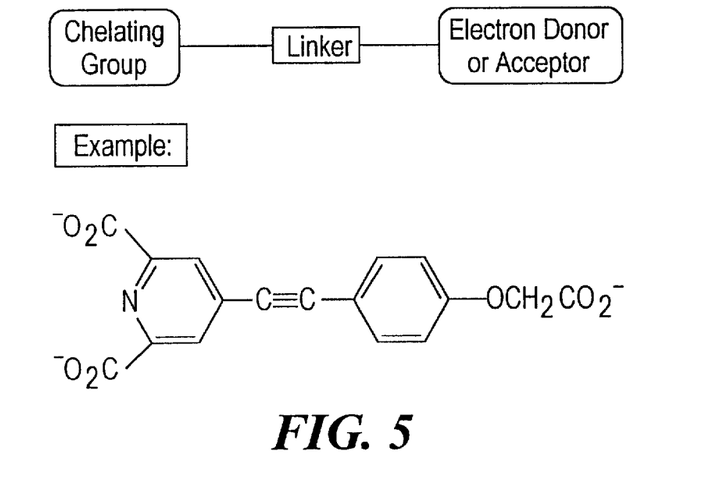
FIG. 5 illustrates the structural concept of introduction of a charge-transfer feature for ligands.

In another embodiment of the present invention, ligands having a particular assembly of substituent groups act as effective light absorbing agents when chelated with various metal groups. A metal-coordinating group is bonded to a linker group that is in turn attached to electron donor or acceptor groups. For illustration, we have used the known dipicolinic acid (DPA) functionality as coordinating group and a triple bond as linker (FIG. 5). For further illustration we have envisioned an electron donor terminal group as the "redox active" part of the structure. The resulting chromophore is modified in such a way as to produce a charge-transfer (CT) character to the low-lying pi-pi* transition for the conjugated ligand.

This CT feature is illustrated in the examples of FIG. 1 in which four ligands incorporate an electron donor moiety in the distal aromatic ring (chelates 2,3,4,6). Desired shifts in wavelength that are due to the introduction of CT character to the ligand transition can be brought about by the incorporation of a variety of electron donor or acceptor groups with various linkers. The latter linking moieties may consist of, but are not limited to, groups that provide a degree of pi electron conjugation such as alkene (C=C), alkyne (C≡C), aryl, azo (N=N); in the parent structure the linking group would be absent. Substituent groups that would be classified as electron donors include, but are not limited to, aryl groups further altered with one or more electron donating substituents such as —OH, —OR, —O—, —$NH_2$, —$NR_2$, $CO_2$—, and $SO_3$. Modifying groups that would be classified as electron acceptors include, but are not limited to, aryl groups further modified by nitro, quinone, carbonyl, ketone, aldehyde, sulfonyl groups, or carboxylic acid derivatives.

Figure 4:
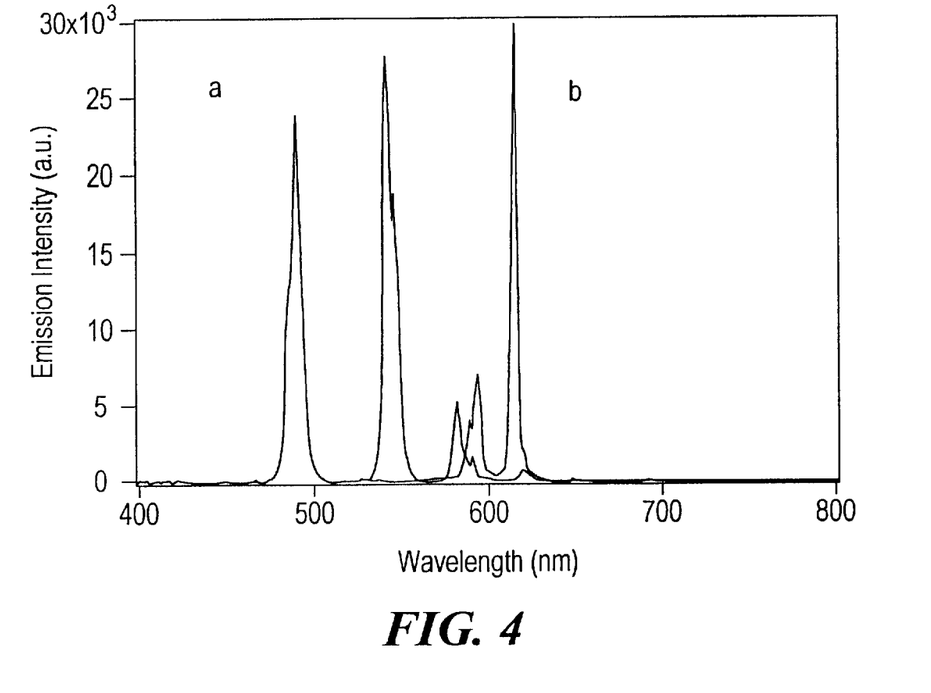
FIG. 4 provides spectral data for two dyes using selective excitation in the UV for producing distinguishable luminescence in the visible (Luminescene spectra for (a) terbium tris (2, 6- pyridinedicarboxylate), and (b) chelate 5 applied to paper and selectively excited at 270 nm and 340 nm, respectively.

The luminescent signal that constitutes a covert label under several embodiments has a combination of innovative features. As shown in FIG. 4 for europium and terbium chelates, luminescence occurs in relatively narrow lines that are better resolved than the fluorescence that is commonly observed for conventional dyes. Chelates show low absorptivity in the visible region, so that marks are not visible to the naked eye. Absorption and luminescence data for chelates 1–6 in solution are shown in Table 1.

Luminescence can be observed by combining two dyes and using selective excitation in the UV as shown in FIG. 4 for a combination of europium and terbium chelates. The present description is not intended to limit the chelates to the use of europium and terbium lanthanides, but encompasses other elements in the lanthanide series, for example, gadolinium and samarium. This assortment of chelates, therefore, provides luminescent materials with windows of utility that span the visible spectrum (400–700 nm) and extends the method of marking to near-infrared wavelengths (700–1100 nm). The present invention does not, however, limit the chosen metal to the lanthanide series of chemical elements. A variety of metal elements are contemplated, and the compositions of the present invention may comprise any type of metal elements.

In the prior art regarding security features that depend on chelates, photodecomposition of inks or films has not been properly considered. In studies relevant to the issue of photostability, the photochemistry of 1,3-diketonate chelates of transition metals has been examined and ascribed to the fragmentation or loss of organic ligands, ligand rearrangement (isomerization), and redox changes at the metal center (R. L. Lintvedt, in "Concepts of Inorganic Photochemistry," A. W. Adamson and P. D. Fleischauer, Eds., Wiley-Interscience, New York, 1975).

Certain classes of chelates show relative instability when compared to chelates utilized in embodiments described herein. Data regarding light stability are provided in Table 2. These results encompass experiments involving the behavior of chelates in films or ink jet prints, as well as solution media. The principal result is that the europium chelates that incorporate the ligands of FIG. 1 are more robust than commonly employed chelates of the 1,3-diketone variety.

Luminescence lifetime data are compiled in Table 3 that show the versatility of the method in terms of application to different substrates/surfaces. The ability to apply chelates from both water-based liquids and solutions of organic solvent is an important feature.

Figure 6:
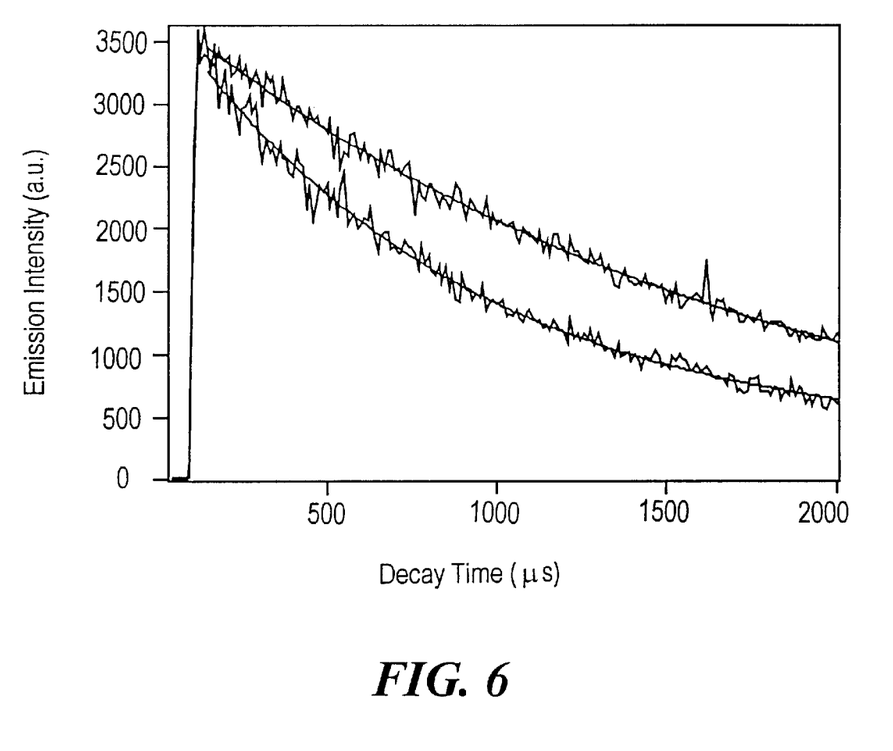
FIG. 6 provides a plot of luminescence decay for chelate 4 on paper (lower curve) and for the application medium of 4 with the addition of a luminescence lifetime modifier, 4-methylimidazole (on plain paper (pH 8.5). $\lambda_{exc}=337$ nm; $\lambda_{lum}==615$ nm).

Security features will display not only a physical image and a color (luminescence wavelength) upon interrogation. A critical additional level of security is associated with "lifetime imaging"—i.e., a covert signature will also include a well defined luminescence decay time, a distinct but adjustable property of each chelate and the medium in which it resides. Lifetime imaging is carried out using pulsed light excitation for sampling. The results of recording lifetimes for two samples are shown in FIG. 6.

The success of lifetime imaging as a security feature depends critically on two factors: (1) the reproducibility of lifetimes for a given sample (the combination of chelate, the medium with which it is applied, and the substrate); and (2) the ability to alter lifetimes in a systematic manner by "tuning" the application medium. The lifetime data shown in Table 4 confirm that both of these criteria are met. The variance in lifetimes is based on the computed average deviation of data based on 3–4 independent measurements of single exponential decays. Thus, lifetimes recorded for a single composition of chelate/medium and substrate are shown to be reproducible to within +5%.

In order that lifetimes be adjustable and therefore part of a matrix of information that is retained in a luminescent security feature, further alteration in the photophysical properties of chelates is required. The inventors have adopted a strategy in which luminescence lifetime modifiers to the application media for a set of chelates are introduced. Three classes of modifiers have been identified that are suitable for altering the lifetime of chelates. The first class relates to the molecule, imidazole, and by extension, structures having the imidazole ring, including the amino acid, histidine, and its derivatives, N-aryl or N-alkyl imidazoles, and annulated structures in which additional aromatic rings are fused (e.g. benzimidazole and the like). For example, stable coordination complexes in the solid state of the lanthanides, europium, ytterbium, and cerium, and N-methylimidazole have been reported; see Evans, J.Coord Chem. 34:229 (1995).

While the present invention can be successfully utilized without understanding the precise mechanisms, the changes that are observed for emission intensities and lifetimes upon addition of imidazole to solutions of chelates before application are believed to be related to the change in number of water molecules remaining at coordination sites that are responsible for luminescence quenching.

Again, without limiting the present invention to any particular mechanism, the effectiveness of imidazole and its simple derivatives as ancillary coordinating ligands might be explained on the basis of the ability of the heterocylic ring nitrogen to act as an electron pair donor; i.e. the imidazoles, being more effective Lewis bases then water, will effectively compete for metal coordination sites. Such factors should be taken into consideration when selecting candidate compounds as possible modifiers (e.g. selecting candidate luminescent enhancers), keeping in mind potential steric requirements of the modifying ligand. With such factors in mind, one can readily screen such candidate compounds using the methods described herein and determine whether such compounds are suitable modifiers.

The second class of luminescence lifetime modifiers is illustrated by the amino acid, iminodiacetic acid. Molecules of the amino acid class are known to promote stable coordination sites to metal centers.

The systematic modification of lifetimes that can be brought about by addition of imidazole or amino acid ligating agents to chelate reagents (Table 4). While the results derive from the application of luminescent chelates on paper, similar effects have also been observed for solution media. The data in sum demonstrate that lifetimes can be altered, typically 25–100%, on the addition of a luminescence lifetime modifier. Another interesting feature of the luminescence data is a subtle change in peak emission intensity that is observed for the principal lanthanide emission bands on addition of a luminescence lifetime modifier. For example, addition of imidazole brings about a change in the intensity ratio for luminescent signals centered at 592 and at 614 nm. This determination is consistent with the finding that the electric dipole character for the $^5DO^2\ ^7F2$ band (612 nm) is more sensitive to the ligand field; Blasse, Adv. Inorg. Chem., 35, 319 (1990).

A third class of luminescence lifetime modifier is most efficacious in situations in which a chelate is applied via an organic solvent. This type of composition of security ink is most appropriate for marking materials comprised of conventional plastic (e.g. vinyl polymer and polyester). One luminescence lifetime modifier for this type of substrate is poly(vinyl acetate) (PVA), a well known commercial alkene polymer having a molecular weight in the range of 10,000–500,000 KD. The inventors have demonstrated that for europium chelates that employ ligands of the 1,3-diketone class, the luminescence intensity is reduced and emission lifetimes are shortened for marking inks that utilize common solvents, including dichloromethane, chloroform, acetone, or ethyl acetate. Increases of 30–40 fold in luminescence intensity and lifetime are observed for ink compositions that include moderate concentrations of PVA (mM range).

The effect of modifying emission lifetimes is ascribed to the role that can be played by a polydentate ligand (PVA or similar polymer) in occupying coordination sites on lanthanide metal centers, replacing small solvent molecules that lead to faster non-radiative decay of chelate excited states. Other polymers that could play a similar role include, but are not limited to, vinyl polymers with side chains composed of ester, ketone, amide, or carboxylic acid groups. Polyester or polyamide structures, including biopolymers such as peptides and proteins, are proposed also as alternate structures for the desired metal coordination. Examples of goods that would be most appropriately marked using the formulation of organic solvent, chelate, and lifetime modifying agent include, but are not limited to, credit or identification cards, packaging for pharmaceutical or software, other forms of plastic wrap, and hard plastic compositions found in autos or aircraft and in games and toys.

The addition of one luminescence lifetime modifier to a set of chelates in effect multiplies the number of unique luminescent reagents by two or more, depending on the effect of different concentrations of the added modifying reagent. The matrix that finally develops is quite robust, employing a wide range of adjustable parameters. The choice of metal determines the wavelength regime in the visible and near-infrared for interrogation. The choice of chelating ligand controls the base lifetime for a particular metal and substrate, with reasonable variations that can range by as much as a factor of 10 (generally, 0.2–2.0 msec). Further adjustment in the luminescent signal is accomplished by addition of a luminescence lifetime modifier (e.g. imidazole, PVA). Still further differentiation in the security feature can be made on the basis of the ratio of vibronic spectral intensities for a particular chelate; i.e, a ratio of emission peak heights can be measured using a steady irradiation source or pulsed excitation (e.g. for europium chelates, $\lambda$=ca. 592 and 612 nm). The combination of multi-color, multi-decay-time interrogation offers unprecedented versatility in terms of systematic alteration of covert identifiers.

One embodiment of the present invention is a mixture comprising first and second compounds in a solvent, the first compound comprising a lanthanide chelate and second compound comprising a luminescence lifetime modifier.

Another embodiment of the present invention is a composition comprising a mixture deposited on a substrate, the mixture comprising a lanthanide chelate and a luminescence lifetime modifier.

Another embodiment of the present invention include methods that provide luminescent compositions comprising a mixture deposited on a substrate, where the mixture comprises a lanthanide chelate and a luminescence lifetime modifier, a device for measuring luminescence lifetimes. The method is contemplated in one embodiment to involve measuring the luminescence lifetime of the luminescent composition using the device. In another embodiment, a device to detect wavelengths of visible or near infrared radiation is employed.

The luminescence lifetime modifiers of the present invention may be a luminescence enhancer, and the lanthanide chelate may be comprised of a lanthanide and a ligand, with the ligand selected from, although not limited to, 1,3-diketones, polypyridines, and polycyclic azaaromatic compounds. The lanthanide of the present invention may be selected from, but not limited to, gadolinium, samarium, neodymium, ytterbium, cerium, terbium and europium, while the solvent may be selected from, but not limited to, water, ethanol, acetonitrile, dichloromethane, tetrahydrofuran, dimethylformamide, and 1,5 pentanediol. The luminescence lifetime modifier may be selected from, but not limited to imidazoles, amino acids, alkene polymers, polyesters, or biopolymers, and the mixture of the present invention may be deposited on a substrate selected from, but not limited to, paper (including, but not limited to, currency, checks, stocks and bonds) leather, cloth, plastic, glass and metal. The mixture may be depositing by a variety of techniques such as brushing, spraying, dripping, printing, copying, writing and doping.

EXPERIMENTAL

The following examples serve to illustrate certain embodiments and aspects of the present invention and are not to be construed as limiting the scope thereof.

Example 1

The Synthesis of Novel Ligands

Figure 3:
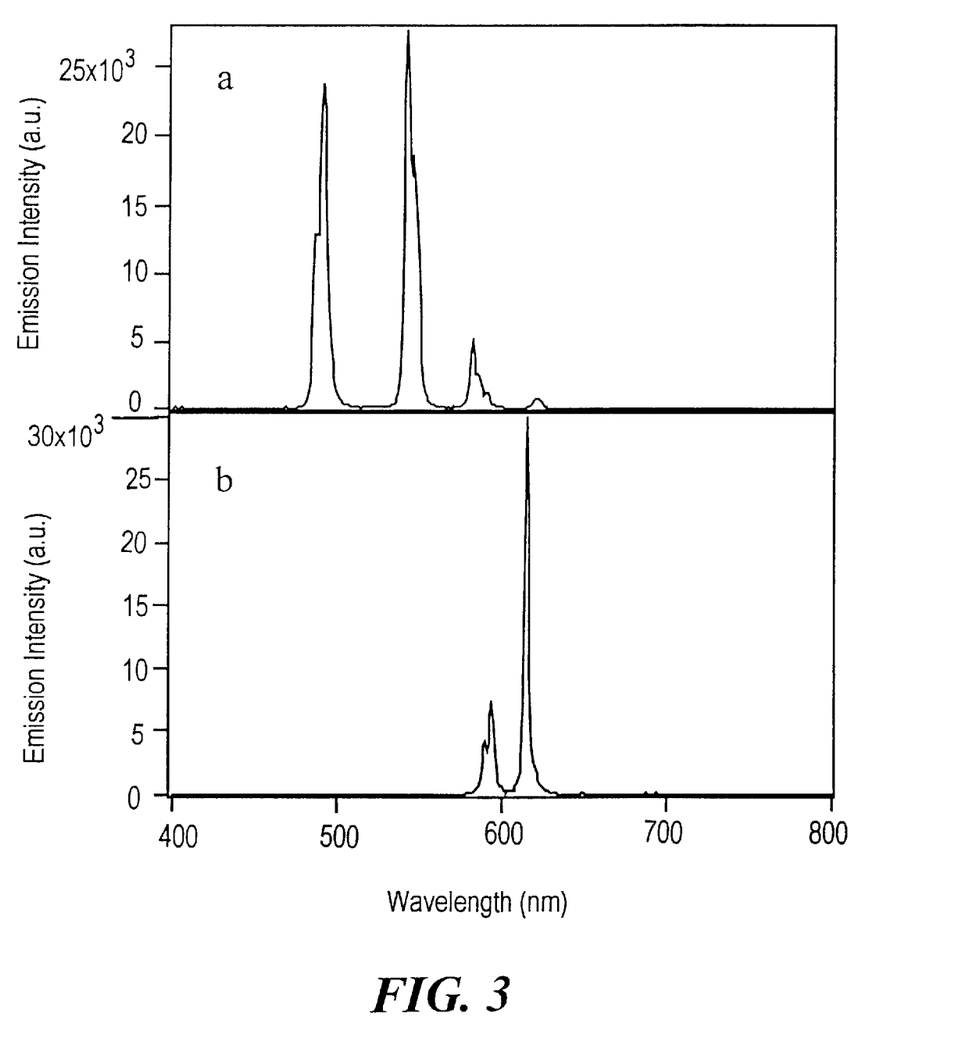
FIG. 3 provides luminescence spectral data for terbian chelate (a) and europium chelate (b) in aqueous solution (pH 8.5) $\lambda_{exc}=337$nm, [dye] = 20 $\mu$M).

In this example, six new ligands have been synthesized (shown in FIG. 1), and their corresponding chelates with europium and terbium ions have been investigated. The europium chelates with the ligand 5 and 6 demonstrate very bright luminescence under the ultraviolet irradiation of 360 nm. The absorption spectra and excitation spectra show the ligand 6 responds to more red-edge 15–20 nm excitation than the ligand 5. The analogous chelates of ligands 5 and 6 with terbium shows distinctive luminescence at 490 and 545 nm (FIG. 3). The ligands were synthesized as follows.

4-(4-methoxyphenylethynyl)-2, 6-pyridinedicarboxylic Acid.

4-Methoxyphenyltrimethylsilylacetylene (8.2 g, 39 mmol) was dissolved in 100 mL of methanol with $K_2CO_3$ powder (0.5 g, 3.6 mmol). The mixture was stirred at room temperature for 4 hr. After the solvent was removed, 50 mL of water was introduced and the mixture was neutralized with dilute hydrochloric acid. The crude product, 4-methoxyphenylacetylene, was extracted with chloroform (2×50 ml) and purified by column chromatography (silica gel) using 3% chloroform/hexane (96%). $^1$HNMR (CDCl3), d 7.39 (d, 2H), 6.81 (d, 2H), 3.77 (s, 3H), 2.96 (s, 1H). Diethyl 4-bromo-2,6-pyridinedicarboxylate (2.0 g, 10 mmol) was dissolved in 70 mL of dry THF and 50 ml of anhydrous triethylamine with $PdCl_2$ (75 mg), $PPh_3$ (200 mg) and CuI (120 mg). The mixture was deaerated with argon for 5 min and 2.0 g of methoxyphenylacetylene (15 mmol) was introduced. The mixture was stirred under an atmosphere of argon at 55° for 6 hr. The solvent was removed, and the residue was treated with water and extracted with chloroform (2×75 ml). The crude product from the dried organic extract was purified by column chromatography (silica gel— 10% ethyl acetate/hexane). The purified product was recrystallized from 50% chloroform/hexane to yield 1.8 g of white crystals (77%). $^1$HNMR (acetone-d6): 8.23 (s, 2H), 7.61 (d, 2H), 7.01 (d, 2H), 4.41 (t, 4H), 3.85 (s, 3H), 1.38 (q, 6H). Diethyl 4-(methoxyphenylethynyl)-2,6-pyridinedicarboxylate (1.8 g, 5.5 mmol) was dissolved in 100 ml of ethanol with 2.0 g of KOH. The mixture was stirred at room temperature for 4 hr. After solvent was removed in vacuo, 80 ml of water was added to the residue, and the solution filtered. The filtrate was acidified with dilute hydrochloric acid. The precipitate that resulted was filtered and dried in air, yielding 1.3 g of a white solid, 4-(4-methoxyphenylethynyl)-2,6-pyridinedicarboxylic acid: mp>300° C. $^1$HNMR ($D_2$ONaOD), δ 8.16 (s, 2H), 7.58 (d, 2H), 7.00 (d, 2H), 3.77 (s, 3H).

4-[4-(Carboxymethyloxy)phenylethynyl]-2,6-pyridinedicarboxylic Acid.

Diethyl 4-bromo-2, 6-pyridinedicarboxylate (1.1 g, 5.5 mmol) was dissolved in 75 ml of dry THF and 35 ml of anhydrous triethylamine with $PdCl_2$ (55 mg), $PPh_3$ (200 mg) and CuI (100 mg). The mixture was deaerated with argon for 5 min, and 1.5 g of ethyl 4-(ethynyl)phenoxyacetate (7.7 mmol) was introduced. The mixture was stirred under an atmosphere of argon at 55° for 6 hr. After the solvent was removed in vacuo, the residue was treated with water and extracted with chloroform (2×75 mL). The crude product from the organic extract, diethyl 4-(methoxyphenylethynyl)-2,6-pyridinedicarboxylate, was purified by column chromatography (silica gel; 10% ethyl acetate/hexane). The purified product was recrystallized from 50% chloroform/hexane to yield 1.0 g of white crystals (72%). $^1$HNMR (acetone-d6): 8.21 (s, 2H), 7.62 (d, 2H), 7.04 (d, 2H), 4.80 (s, 2H), 4.41 (q, 4H), 3.72 (s, 3H) 1.41 )(q, 6H). The diester product (0.3 g) was dissolved in 50 ml of methanol with 0.8 g of KOH. The mixture was allowed to stir at room temperature for 3 hr. The solvent was removed and the residue was treated with 30 ml of water and acidified with dilute hydrochloric acid. The product, 4-[4-(carboxymethyloxy)phenylethynyl)]-2,6-pyridinedicarboxylic acid, was obtained as a white precipitate and thoroughly dried (75% mp>300° C.). $^1$HNMR ($D_2$ONaOD): δ 7.83 (s, 2H), 7.39 (d, 2H), 6.76 (d, 2H, 4.32 (s, 2H).

4-(3,4-dicarboxyphenylethynyl)pyridine-2, 6-dicarboxylic Acid.

To an Ar-purged mixture of diethyl 4-bromopyridine-2, 6-dicarboxylate (1.2 g, 4.0 mmol) dissolved in 100 ml of dry THF and 25 mL of triethylamine with $PdCl_2$ (30 mg), CuI (50 mg), and $PPh_3$ (200 mg) was introduced dimethyl 4-ethynylphenyl-1,2-dicarboxylate. The mixture was stirred under Ar at 55° for 6 hr. The solvents were removed and the residue dissolved in chloroform (75 ml) and washed with water. The crude product was purified by column chromatography (silica gel; 4:1 chloroform/hexane) and recrystallized from 1:1 chloroform/hexane (76%). $^1$HNMR (CDCl$_3$), 8.28 (s, 2H), 7.78 (d, 1H), 7.66 (d, 1H), 7.59 (dd, 1H), 4.43 (q, 4H), 3.84 (s, 3H), 3.83 (s, 3H), 1.42 (t, 6H). The tetraester (0.8 g, 1.8 mmol) was dissolved in 50 ml of ethanol with 1.0 g of KOH. After the mixture was stirred at room temperature for 3 hr, the solvent was removed and the residue dissolved in water and filtered. After the filtrate was acidified with dilute HCl, the product, 4-(3,4-dicarboxyphenylethynyl) pyridine-2,6-dicarboxylic acid, was obtained as a white precipitate (86% mp>300° C.). $^1$HNMR ($D_2$ONaOD): δ 7.95 (s, 2H), 7.57 (s, 1H), 7.49 (d, 1H), 7.36 (d, 1H).

4'Phenylethynyl-(2,2':6',2")-terpyridine-6,6"-dicarboxylic Acid.

To an Ar-purged mixture of dimethyl 4'-bromo-(2,2':6', 2")-terpyridinedicarboxylate (1.0 g, 2.3 mmol) dissolved in 150 m of dry THF and 25 mL of triethylamine with $PdCl_2$ (50 mg), CuI (150 mg), $PPh_3$ (0.3 g) in a three-necked flask was added 1.5 g of phenylacetylene (14.7 mmol). The resulting mixture was stirred at 55° for 6 hr. The solvent was removed and the residue was treated with 100 mL of water followed by extraction with chloroform (2×75 mL). The crude product was purified by column chromatography (silica gel, CHCl$_3$). $^1$HNMR (CDCl$_3$): δ 8.78 (d, 2H), 8.69 (s, 2H), 8.16 (d, 2H), 8.00 (t, 2H), 7.60 (m, 2H), 7.36 (m, 3H), 406 (s, 6H).

The diester (0.3 g, 0.67 mmol) was dissolved in 20 ml of ethanol with 0.3 g of KOH. The mixture was stirred at room temperature for 3 hr. After rotary evaporation of the solvent, the residue was treated with 30 ml of water. The resulting solution after filtration was acidified with dilute HCl and the final product obtained as a white precipitate (67% yield, mp=262° C.) $^1$HNMR (DMSO-d6): δ 8.85 (d, 2H), 8.81 (d, 2H), 8.59 (d, 2H), 8.18 (d, 2H), 8.15 (s, 2H), 8.11 (t, 2H), 7.45 (t, 1H).

4'-methoxyphenyletynyl-(2,2':6',2")-terpyridine-6, 6"-dicarboxylic Acid.

To an Ar-purged mixture of dimethyl 4'-bromo-(2,2':6', 2")-terpyridine-6,6"-dicarboxylate (1.3 g, 3.0 mmol) dissolved in 105 mL of dry THF and 15 mL of dry triethylamine with $PdCl_2$ (65 mg), CuI (150 mg), $PPh_3$ (0.3 g) was introduced 4-methoxyphenylacetylene (1.8 g, 13.6 mmol). The resulting mixture was stirred at 50° for 6 hr. The solvents were removed and residue was treated with water and extracted with chloroform. The crude product was purified by column chromatography (silica gel; 1:1, chloroform/hexane). $^1$HNMR (CDCl$_3$): 8.78 (d, 2H), 8.65 (s, 2H), δ 8.15 (d, 2H), 7.99 (t, 2H), 7.53 (m, 2H), 6.90 (m, 3H), 4.04 (s, 6H), 3.83 (s, 3H).

The diester (0.6 g, 1.2 mmol) was dissolved in 30 mL of ethanol with 0.8 g of KOH. The mixture was stirred at room temperature for 3 hr. After the solvent was removed, the residue was treated with water and acidified with dilute HCl; the final product was obtained as a white precipitate (62% mp>300° C.). $^1$HNMR (DMSO-d6) δ 8.33 (d, 2H), 7.88 (d, 2H), 7.61 (d, 2H), 7.57 (s, 2H), 7.52 (d, 2H), 6.96 (d, 2H), 3.74 (s, 3H).

Example 2

General Procedure for the Synthesis of Europium and Terbium Chelates

One equivalent of europium chloride hexahydrate or terbium chloride in a minimal amount of water and three equivalents of ligand in basic solution (pH~9) were mixed together. The clear solution that was obtained can be used with proper dilution for photophysical measurements or sprayed onto paper and dried at 140°. The chelate solutions could also be used by filling standard ink jet cartridges (e.g. HP 516410A).

Additional data on individual chelates: On suspension of ligand 4 (3 mmol) in water(30 mL) and treatment with dilute NaOH (0.1 M) to achieve pH 9, a clear solution was obtained. Europium chloride $EuCl_3$ (1 mmol, in 5 mL of water) was added, and pH adjusted again to pH 8.5. The solution was allowed to evaporate slowly (over a period of several days) to produce 0.86 g of white crystals (70%) (m.p.>300°). $^1$HNMR ($D_2O$): d 7.84 (s, 2H), 7.40 (d, 2H), 6.81 (d, 2H), 3.63 (s, 3H). The chelate of ligand 2 and $Eu^{3+}$ was synthesized following a similar procedure (Yield: 64%; mp>300° C.). $^1$HNMR ($D_2O$) d 7.91 (s, 2H), 7.46 (d, 2H), 6.68 (d, 2H), 438 (s, 2H).

Example 3

Combining Novel Chelate and Substrates

Lanthanide chelates can be applied to a large variety of surfaces, including plastic, glass, metal, paper, synthetic fabric, cotton, and wool. For example, bright luminescence was observed under UV illumination using chelates that included europium tris-(1-naphthoyltrifluoroacetonate) [Eu$(NRA)_3$] and chelates 1 and 2 with particular sample preparations. An advantageous composition required ethanol solutions combined with the organic polymer, poly(vinyl acetate) (PVA) (avg. molecular weight=167,000 KD) dissolved in either dichloromethane, acetone, or ethyl acetate solution. Specific examples include: (a) Eu$(NRA)_3$ in ethanol (0.5 ml of a 100 μM solution) mixed with 5 ml of 20% (w/v) PVA in ethyl acetate. After a few drop of the colorless solution was applied to a plastic identification card that was subsequently dried in air, bright red luminescence was observed under excitation with ultraviolet light at 285–385 nm; (b) chelate 2 in ethanol (0.5 ml of a 100 μM solution) mixed with 5 ml of 20% (w/v) PVA in dichloromethane. Similar application to a plastic card resulted in the observation of red luminescence. This luminescence displayed the characteristic luminescence maximum near 615 nm, with a luminescence excitation peak at 350 nm.

Other examples include application of (a) chelate 1 applied as an aqueous solution with 10% (w/v) poly(vinyl pyrrolidone) (PVP) (MW: 10,000) to aluminum foil and (b) chelate 4 applied as an aqueous solution with 1,5-pentanediol (15% v/v) to the interior pages of an American passport. Another example involves the application of chelate 2 or terbium 4'-phenylethynyl-(2,2':6'2")-terpyridine-6,6"-dicarboxylate (8) to polyester threads (2 mm strands). Thread material was dipped into an aqueous solution of the europium chelate to which had been added PVP (10% w/v) or poly(vinyl alcohol) (MW: 10,000) (10% w/v) and dried in an oven at 150°. Red luminescence (615 nm) was observed under excitation in the ultraviolet at 280–385 nm for chelate 2, whereas bright green luminescence (545 nm) was observed for the terbium chelate.

Example 4

Figure 7:
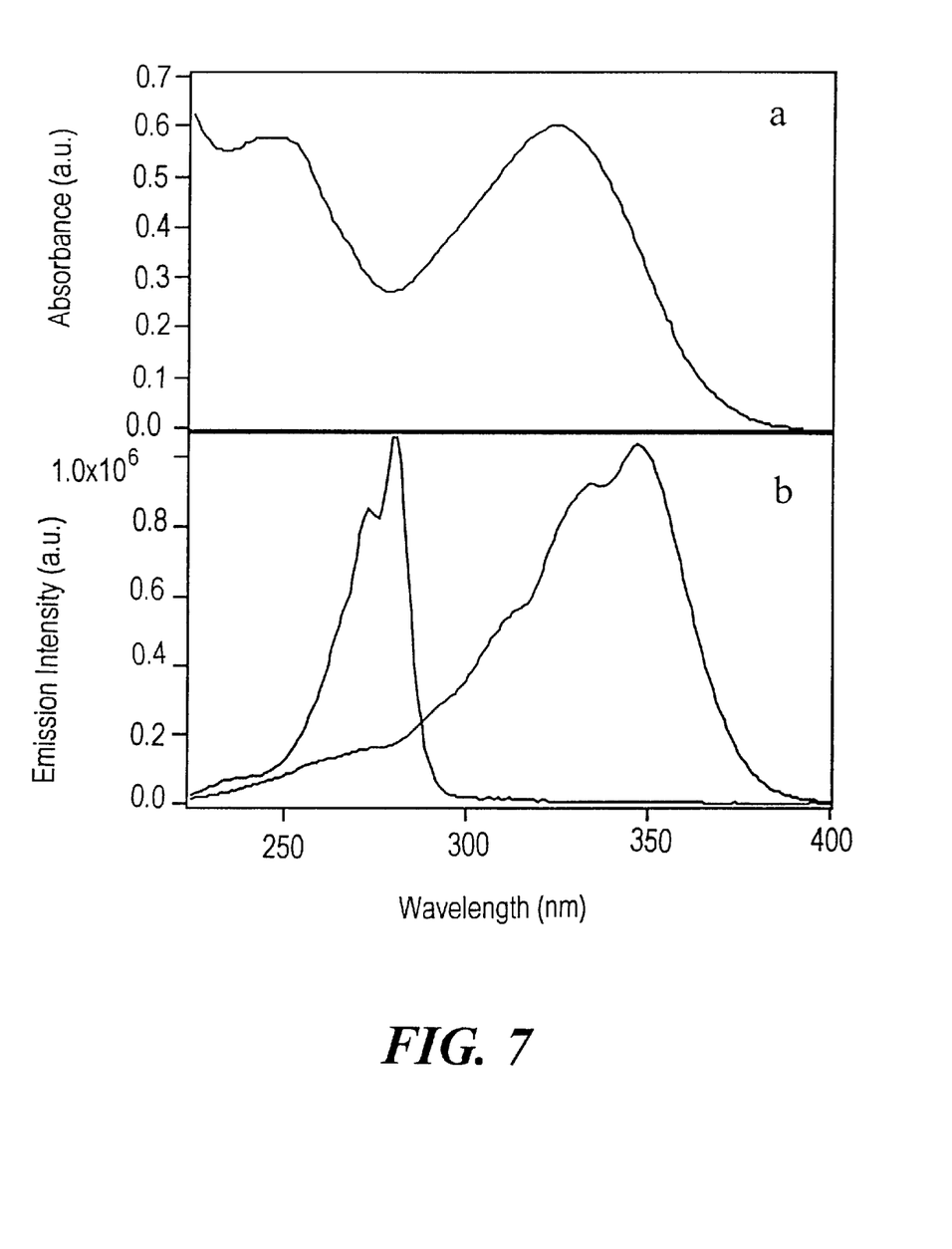
FIG. 7 provides absorption and luminescence excitation spectra for comparison of ligand modifications.

Ligand Modification: Charge Transfer Absorption Features and Stabilization Against Photodegradation Chelate 4 was prepared according to the design of FIG. 5 whereby an electron donor moiety is attached to an alkyne linker group which is in turn attached to a pyridine-2,6-dicarboxylic acid ligating group. The absorption spectrum for 4 is provided in FIG. 7a and other photophysical data in Table 1. The results illustrate a red-shift of the absorption band in the near ultraviolet. The favorable alteration in absorption for 4 is further illustrated in a comparison of its excitation spectrum (FIG. 7b) with that of the parent chromophore associated with the europium chelate, tris-(2,6-pyridinedicarboxylic acid)Eu(III) (7) or with the partially modified chromophore associated with 1 (Table 1). Chelate 4 was also associated with high photostability as demonstrated in experiments of comparative stability as summarized in Table 2.

For these experiments, 200 μM samples of chelates prepared in water (pH 8.5) were applied to paper (e.g. Hammermill Tidal DP; long grain 10M-S20/50, 75 g/m$^2$) and exposed to intermittent sunlight filtered by common exterior glass for periods of days extending into months, during the period, September, 1998–May, 1999. For this comparison, the chelates denoted 1'–5' were used; these were composed of the europium complexes of the diketonate class encompassing, for example, the ligands, naphthoyltrifluoroacetonate and benzoyltrifluoroacetonate.

Example 5

Ink-jet Printing

To 20 ml of a concentrated aqueous solution of europium 4-carboxymethyloxy)phenylethynyl-2,6-dicarboxylate (4) was added 1,5-pentanediol and trimethylolpropane (10–15% w/w). The colorless solution was filtered to remove any particles. The solution was used to fill standard Hewlett-Packard (HP) 51641A cartridges; and images were printed on paper using an HP 855 Cxi printer.

Example 6

Control of Luminescence Lifetimes Through the use of Luminescence Lifetime Modifiers Lifetimes could be adjusted in a regular way when compositions were altered using a series of modifying lanthanide ligating agents. Table 4 includes examples of measured lifetimes obtained from chelate compositions that are based on chelates 1–6 to which three selected luminescence lifetime modifiers have been added. The compositions were composed of chelates (0.20 mM) and luminescence lifetime modifiers (1.0 mM) in water (pH=9.0). These compositions were applied to paper (e.g. Hammermill Tidal DP; long grain 10M-S20/50, 75 g/m$^2$) and excited at 337 nm using nitrogen laser excitation in a fluorimeter (right angle illumination). Samples were monitored at 545 nm (terbium chelates) and at 615 nm (europium chelates). Individual lifetimes were recorded based on the fitting of first order decay curves ($x^2$=1.05–1.1), and were reproducible based on samples prepared in duplicate, and decay curves analyzed in triplicate (±5%).

Example 7

Composition Including a Polymer as Luminescence Lifetime Modifier

The europium tris-(1-naphthoyltrifluoroacetonate) [[Eu(NRA)$_3$] chelate was applied by micropipetting: 100 µM of Eu(NRA)$_3$ in dichloromethane on paper and the lifetime recorded for this sample was 0.5 ms ($\lambda_{exc}$=337 nm); The [Eu(NRA)$_3$] chelate was applied again to the same Tidal DP paper using a 100 µM sample of Eu(NRA)$_3$ with added luminescence lifetime modifier, 20% (w/v) poly(vinyl acetate). The mission lifetime recorded for this tagged paper was increased to 1.0±0.1 ms.

From the above description and examples, it should be clear that the present invention provides improved luminescent compositions and methods for their comparison. Accordingly, this invention is not limited to the particular embodiments disclosed, but is intended to cover all modifications that are within the spirit and scope of the invention as defined by the appended claims.

TABLE 1

Absorption and luminescence parameters for europium chelates[a]

| Chelates | $\lambda_{max (abs)}$ | $\epsilon_{max}$ | $\lambda_{max (lum)}$ | $\tau_{lum}$ |
|---|---|---|---|---|
| 1 | 308 nm | 17400 | 615 nm | 0.97 ms |
| 2 | 326 nm | 16600 | 615 nm | 1.02 ms |
| 3 | 317 nm | 17200 | 614 nm | 1.01 ms |
| 4 | 337 nm | 19300 | 615 nm | 0.97 ms |
| 5 | 339 nm | 26000 | 614 nm | 0.36 ms |
| 6 | 352 nm | 24200 | 615 nm | 0.43 ms |

[a]Aerated water solutions, pH 8.5; [chelate] = 40 µM; $\lambda_{exc.}$ = 337 nm for lifetime $\tau_{lum}$ measurements; $\tau_{lum}$ recorded by monitoring emission at 615 nm.

TABLE 2

Light stability of lanthanide chelates

| Chelates | Irradiation Method | Relative Stability |
|---|---|---|
| 1' | Natural light Source | 1 Days |
| 2' | Natural light Source | 2 Days |
| 3' | Natural light Source | 7 Days |
| 4' | Natural light Source | 7 Days |
| 5' | Natural light Source | 9 Days |
| 1 | Natural light Source | >400 Days |
| 2 | Natural light Source | >400 Days |
| 3 | Natural light Source | >100 Days |
| 4 | Natural light Source | >200 Days |
| 5 | Natural light Source | >300 Days |
| 6 | Natural light Source | >300 Days |

TABLE 3

Luminescence lifetime data for lanthanide chelates applied to different substrates

| Chelate | Application medium | Substrate | $\lambda_{lum.}$ | $\tau_{lum.}$ |
|---|---|---|---|---|
| 1 | Water | Plastic | 615 nm | 0.95 ms |
| 2 | Water | Cloth | 615 nm | 1.00 ms |
| 3 | Water | Paper | 614 nm | 0.98 ms |
| 4 | Water | Thread | 615 nm | 1.01 ms |
| 5 | Water | Paper | 614 nm | 0.34 ms |
| 6 | Water | Paper | 615 nm | 0.42 ms |
| 4' | Ethanol | Metal | 614 nm | 0.44 ms |
| 5' | Ethyl acetate | Plastic | 615 nm | 0.41 ms |

TABLE 4

Luminescence lifetime data for chelates

| Chelate | None | Modifiers[a] Imidazole | 4-MI | IDA |
|---|---|---|---|---|
| 1 | 0.97 ms | 1.19 ms | 1.22 ms | 0.44 ms |
| 2 | 1.02 ms | 1.21 ms | 1.37 ms | 0.48 ms |
| 3 | 1.01 ms | 1.23 ms | 1.19 ms | 0.46 ms |
| 4 | 0.97 ms | 1.27 ms | 2.03 ms | 0.60 ms |
| 5 | 0.36 ms | 0.65 ms | 0.54 ms | 0.50 ms |

[a]Modifiers at 1.0 mM concentration, imidazole, 4-methylimidazole (4-MI), and iminodiacetic acid (IDA), were added to an application medium of 200 µM chelate in water (pH 9.0) and applied to plain paper; lifetimes (units of ms) from exponential luminescence decay curves ($\lambda_{exc}$ = 337 nm; l$\lambda_{lum}$ = 615 nm).

We claim:

1. A method for determining the authenticity of a substrate, comprising:
    a) providing: i) a luminescent composition comprising a mixture deposited on said substrate, said mixture comprising a lanthanide chelate; a luminescent lifetime modifier, and a solvent; and ii) a device for measuring luminescent lifetimes; and
    b) measuring the luminescent lifetime of said luminescent composition using said device,
       wherein said solvent is selected from water, ethanol, acetonitrile, dichloromethane, tetrahydrofuran, dimethylformamide, and 1,5 pentanediol.

2. A method for determining the authenticity of a substrate, comprising:
    a) providing: i) a luminescent composition comprising a mixture deposited on said substrate, said mixture comprising a lanthanide chelate, a luminescent lifetime modifier, and a solvent; and ii) a device for measuring luminescent lifetimes; and
    b) measuring the luminescent lifetime of said luminescent composition using said device,
       wherein said luminescent lifetime modifier is polyvinyl acetate.

3. A method for determining the authenticity of a substrate, comprising:
    a) providing: i) a luminescent composition comprising a mixture deposited on said substrate, said mixture comprising a lanthanide chelate and a luminescent lifetime modifier; and ii) a device wherein said device detects wavelengths of visible or near infrared radiation; and
    b) measuring the wavelength of said luminescence of said luminescent composition using said device,
       wherein said luminescent lifetime modifier is polyvinyl acetate.

4. A taggant composition comprising a lanthanide chelate and a luminescent lifetime modifier, wherein said luminescent lifetime modifier is an imidazole or a di- or tri-dentate aminocarboxylic acid.

5. The taggant composition of claim 4 wherein said luminescent lifetime modifier is iminodiacetic acid.

6. A substrate coated with the taggant composition of claim 4.

7. The substrate of claim 6 wherein said substrate is selected from the group consisting of paper, leather, cloth, plastic, glass and metal.

8. The substrate of claim 6 wherein said coating is achieved by a process selected from the group consisting of brushing, spraying, dripping, printing, copying, writing and doping.

9. A method of tagging products in order to determine their authenticity, comprising:

a. applying a taggant composition, to said product, said taggant comprising a lanthanide chelate and a luminescent lifetime modifier, wherein said luminescent lifetime modifier is an imidazole or a di- or tri-dentate aminocarboxylic acid, b. measuring the luminescence lifetime of the mark on said product, and c. comparing the luminescence lifetime of said mark to the luminescence lifetime of the mark originally placed on said product to determine whether said product is authentic.

10. The method of claim 9 wherein said luminescent lifetime modifier is iminodiacetic acid.

* * * * *

UNITED STATES PATENT AND TRADEMARK OFFICE
CERTIFICATE OF CORRECTION

PATENT NO. : 6,402,986 B1
APPLICATION NO. : 09/354891
DATED : June 11, 2002
INVENTOR(S) : Guilford Jones, II et al.

It is certified that error appears in the above-identified patent and that said Letters Patent is hereby corrected as shown below:

Column 4, line 39, "terbian" should read --terbium--;

Column 4, line 47, "respectively." should read --respectively).--

Column 4, line 56, "modifications." should read --modifications (absorption spectrum of chelate 4 (a), and the excitation spectra of chelate 4 (b-right) and chelate 7 (b-left) (20 $\mu$ M) in aqueous solution (pH 8.5).--

Column 6, line 17, "sites if on" should read --sites on--;

Column 9, line 28, "$^5DO^2\ ^7F2$" should read --$^5D0^2\ ^7F2$--;

Column 11, line 44, "(D$_2$ONaOD)" should read --(D$_2$O/NaOD)--

Column 12, line 4, "(D$_2$ONaOD)" should read --(D$_2$O/NaOD)--

Column 12, line 26, "(D$_2$ONaOD)" should read --(D$_2$O/NaOD)--

Column 12, line 28, "4'Phenylethynyl" should read --4'-phenylethynyl--

Column 12, line 29, "Acid" should read --acid--;

Column 12, line 52, "Acid" should read --acid--;

Signed and Sealed this

Fifth Day of December, 2006

JON W. DUDAS
*Director of the United States Patent and Trademark Office*